(12) United States Patent
Hoang et al.

(10) Patent No.: US 8,348,913 B2
(45) Date of Patent: Jan. 8, 2013

(54) SYSTEMS AND METHODS FOR PROVIDING AN ANTISEPTIC APPLICATOR

(75) Inventors: Minh Quang Hoang, Sandy, UT (US); Jonathan Karl Burkholz, Salt Lake City, UT (US); Weston F. Harding, Lehi, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 209 days.

(21) Appl. No.: 12/846,530

(22) Filed: Jul. 29, 2010

(65) Prior Publication Data

US 2011/0066121 A1 Mar. 17, 2011

Related U.S. Application Data

(60) Provisional application No. 61/242,445, filed on Sep. 15, 2009.

(51) Int. Cl.
*A61M 35/00* (2006.01)

(52) U.S. Cl. ............ 604/310; 604/3; 604/403; 604/409; 604/415; 401/205; 401/134; 401/132

(58) Field of Classification Search .............. 604/3, 403, 604/409, 310, 415; 401/205, 134, 132
See application file for complete search history.

(56) References Cited

U.S. PATENT DOCUMENTS

| | | | |
|---|---|---|---|
| 4,925,327 A * | 5/1990 | Wirt | 401/205 |
| 5,147,337 A | 9/1992 | Plone | |
| 5,308,180 A | 5/1994 | Pournoor et al. | |
| 5,435,660 A | 7/1995 | Wirt | |
| 5,509,744 A | 4/1996 | Frazier | |
| 5,713,843 A * | 2/1998 | Vangsness | 604/3 |
| 6,371,675 B1 | 4/2002 | Hoang et al. | |
| 6,391,014 B1 * | 5/2002 | Silverman | 604/415 |
| 6,536,975 B1 | 3/2003 | Tufts | |
| 6,729,786 B1 | 5/2004 | Tufts et al. | |
| 6,846,297 B2 * | 1/2005 | Lin | 604/1 |
| 6,916,133 B2 | 7/2005 | Hoang et al. | |
| 6,991,394 B2 * | 1/2006 | Tufts et al. | 401/134 |
| 2002/0076258 A1 | 6/2002 | Crosby et al. | |
| 2004/0240927 A1 | 12/2004 | Hoang et al. | |
| 2006/0039741 A1 | 2/2006 | Tufts et al. | |

FOREIGN PATENT DOCUMENTS

WO    WO 2009/076612 A1    6/2009

* cited by examiner

*Primary Examiner* — Tatyana Zalukaeva
*Assistant Examiner* — Andrew J Mensh
(74) *Attorney, Agent, or Firm* — Jeanne Lukasavage; Craig Metcalf; Kirton McConkie

(57) ABSTRACT

An antiseptic applicator device having a reservoir for storing an antiseptic agent, the reservoir being coupled to an applicator pad, and a defeatable membrane being interposed between the reservoir and the applicator pad. Embodiments of the device further include opposing handles, wherein an interior lumen of each handle houses a breakable phial containing a desired solution, and wherein upon moving the handles to a closed position, the phials are broken to release the desired solutions which are then absorbed by the applicator pad.

8 Claims, 15 Drawing Sheets

SYSTEMS AND METHODS FOR PROVIDING AN ANTISEPTIC APPLICATOR

CROSS-REFERENCE TO RELATED APPLICATIONS

This application claims the benefit of U.S. Provisional Application No. 61/242,445 filed Sep. 15, 2009 titled, SYSTEMS AND METHODS FOR PROVIDING AN ANTISEPTIC APPLICATOR. This application incorporates by reference and claims priority to the provisional application.

BACKGROUND OF THE INVENTION

The present invention relates to systems and methods for providing an antiseptic applicator. An antiseptic applicator is used to apply an antiseptic agent to a desired surface thereby preparing the surface for an antiseptic procedure or treatment.

Antiseptic and antibacterial agents are commonly used in the treatment of various injuries, such as cuts and abrasions. These agents are also commonly applied to various surfaces in preparation for sterile or antiseptic procedures. For example, a common pre-operative procedure in the medical industry involves rubbing alcohol, iodine or peroxide on a skin surface to kill bacteria and thus reduce the chance of infection. Other common practices include wiping down a chair or table surface with an antiseptic agent prior to exposing a patient or instruments to the surface.

Typically, an applicator, such as a cotton swab or foam pad, is soaked with an antiseptic that must be poured from a bottle or other container. This step requires that the user remove the lid of the container and the foil seal to access the antiseptic. In an emergency situation, or in a situation where the one of the user's hands is occupied, the user is required to free both hands to access the antiseptic agent. Furthermore, once the bottle or other container is opened, the sterility of the bottle is compromised often resulting in excess waste of otherwise useful antiseptic agent.

Following these steps, the antiseptic is commonly poured into an open, secondary container which provides a pool into which the applicator is dipped or soaked. The open, secondary container may include a dish or small bowl having a large opening through which the applicator is passed. In an emergency situation the user must take caution to prevent bumping or disturbing the secondary container so as to prevent a spill of the antiseptic. In the event that the antiseptic agent is spilled, additional antiseptic must be provided thereby requiring the user to once again access the container or bottle of antiseptic.

In other procedures, an antiseptic agent is applied directly to a surface from the bottle or other container, and is then spread and applied with the applicator. During these procedures, the user must take precautions to control the amount of antiseptic used so as to contain the antiseptic and avoid wasting materials.

For some procedures, a portion of the applicator that contacts the desired surface is held directly in the hand of the user. For example, where the applicator is a wipe and the surface is a table top, the user generally holds the wipe in their hand and rubs the surface with the wipe. The proximity of the user's hand to the table surface presents the danger of contaminating the newly sanitized surface with the user's hand. While the user may choose to wear protective gloves or wash their hands prior to applying the antiseptic, in an emergency situation the user may not have sufficient time to take the necessary precautions.

Thus, while techniques currently exist that are used for applying an antiseptic agent to a desired surface, challenges still exist. Accordingly, it would be an improvement in the art to augment or even replace current techniques with other techniques.

BRIEF SUMMARY OF THE INVENTION

The present invention relates to a safe and convenient handheld applicator device for delivering an antiseptic solution to a desired surface. Some embodiments of the present invention provide an applicator device including a body having a lumen for receiving an antiseptic agent. The body is generally composed of a semi-flexible polymer material capable of being compressed or squeezed by a user. One end of the body is configured to receive a fluid reservoir containing a desired antiseptic solution. Upon coupling the fluid reservoir to the body, the solution within the reservoir is transferred to the lumen of the body. At the other end of the body, the device includes an adapter pad for absorbing and applying the antiseptic solution to a desired surface. The applicator pad generally includes a non-woven or foam pad material suitable for applying the antiseptic solution.

A defeatable membrane is interposed between the lumen of the body and the applicator, such that the antiseptic agent is prevented from contacting the applicator. In some embodiments, the device further includes a handle whereby upon activating the handle the membrane is defeated thereby permitting the antiseptic agent to flow through the membrane and contact the applicator. In other embodiments, the membrane is defeated by simply compressing the body of the device to increase the pressure within the lumen. The increased pressure is released as the membrane is defeated and the antiseptic agent is permitted to flow through the membrane. In other embodiments, the membrane is replaced with a one-way valve that is defeated by increasing the pressure within the lumen of the body.

In some embodiments of the present invention, the applicator is shaped and configured to apply the antiseptic agent to an orifice, such as a mouth or a respirator tube. In other embodiments, the applicator is shaped and configured to apply the antiseptic agent to a generally flat surface such as an I.V. insertion site, a surgical procedure site or a table.

For some implementations of the present invention, the antiseptic applicator device includes a pair of opposing handles coupled to an applicator pad. Each handle includes an interior lumen configured to house a fluid reservoir, such as an ampoule or phial. Each lumen is in fluid communication with the applicator pad, such that as a fluid reservoir is defeated, the fluid contained within the reservoir is released and absorbed by the applicator pad.

In some embodiments, the fluid reservoir of each handle is defeated by simply squeezing or compressing the outer surface of the handle to crush or break the reservoir material. In other embodiments, a wedge point is positioned between the opposing handles such that as the handles are moved to a closed position, the wedge point is driven into or against the fluid reservoirs thereby defeating the reservoirs.

When a fluid reservoir is included in each of two handles, the fluid reservoir of each handle may include the same or different solutions. For example, where the antiseptic agent is a two-part reagent, the fluid reservoir of one handle may include the first part of the antiseptic agent, and the fluid reservoir of the other handle may include the second part of the antiseptic agent. Thus, when the reservoirs are defeated, the first and second halves of the antiseptic agent are mixed to provide the desired antiseptic solution.

In some embodiments, it may be desirable to apply a first solution contained in the fluid reservoir of the first handle prior to applying a second solution contained in the fluid reservoir of the second handle. Thus, some embodiments of the device include a multistep wedge point whereby the first fluid reservoir is defeated based upon a first position of the opposing handles, and the second fluid reservoir is defeated based upon a second position of the opposing handles. Additionally, some embodiments include a layered applicator pad such that contaminated layers of the pad may be removed to provide a fresh, uncontaminated application surface.

Finally, in some embodiments the device includes a membrane having a scored surface that partially defeated in response to lateral force. As the lateral force is increased, additional portions of the membrane are defeated thereby permitting increased flow of the antiseptic agent through the membrane. In other embodiments, the membrane includes a plurality of scorings having various thicknesses and dimensions to progressively defeat the membrane in response to progressive increases in lateral force against the membrane.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict typical embodiments of the invention and are not therefore to be considered to limit the scope of the invention.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
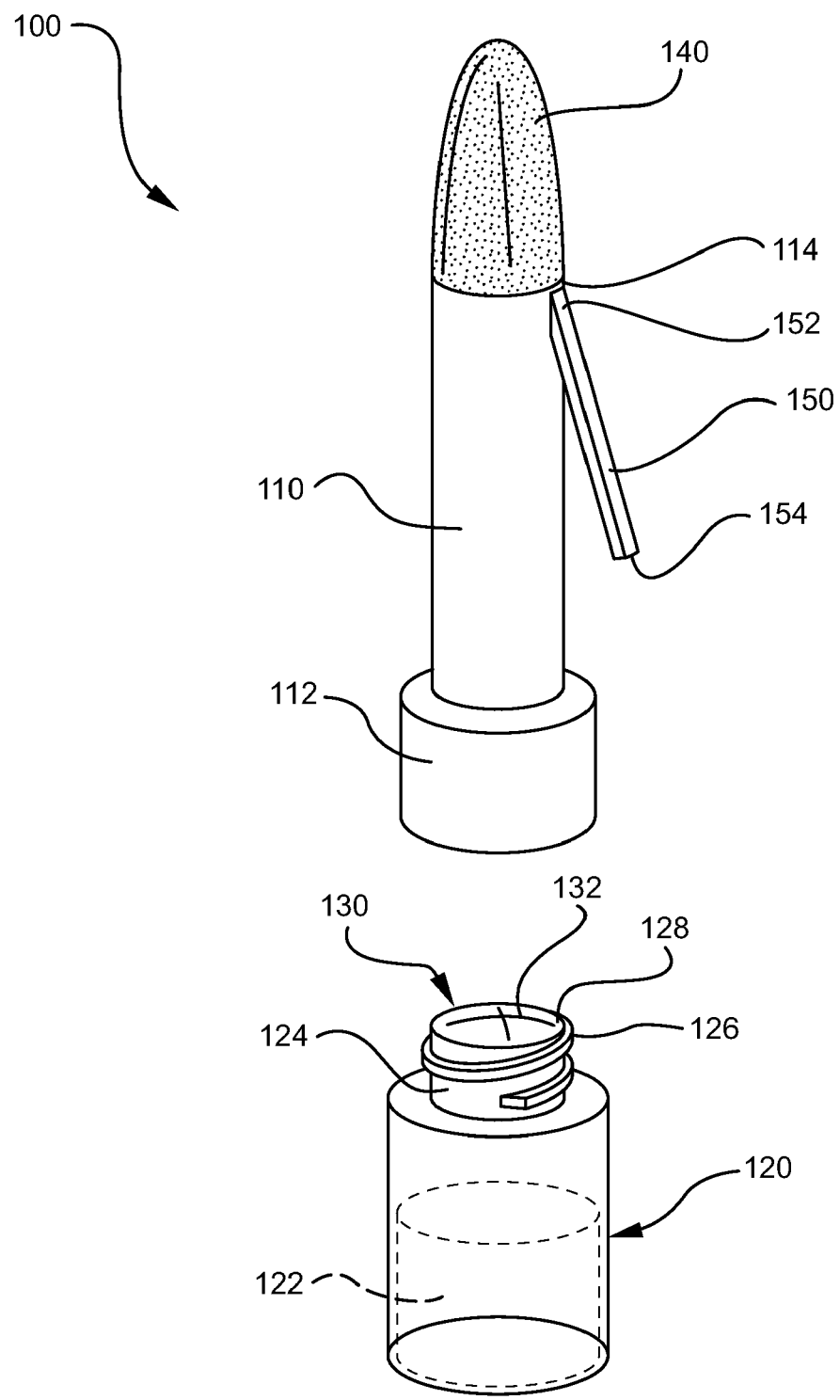
FIG. 1 is a perspective view of an antiseptic applicator device in accordance with a representative embodiment of the present invention.

Referring now to FIG. 1, an implementation of an antiseptic device 100 is shown. Some embodiments of the antiseptic device 100 generally include a body 110, having a proximal end 112 and a distal end 114. The proximal end 112 is generally configured to compatibly receive a reservoir 120 or phial containing an antiseptic agent 122, shown in phantom. In some embodiments, the reservoir 120 contains approximately 0.5-50 mL of the antiseptic agent 122. In other embodiments, the reservoir 120 contains an alcohol-based antimicrobial solution.

For example, in some embodiments an antimicrobial solution in accordance with the present invention includes a 50-95% alcohol solution which further includes additional antimicrobial agents such as CHG, PCMX, triclosan, octenidine, hexachlorophene, PVP-1, iodine, and/or quaterine compounds in the range of 0.05% to 5% w/w. The alcohol is generally selected from at least one of ethyl alcohol, isopropal alcohol, n-propanol alcohol, and mixtures thereof. In some embodiments, the solution further contains dimethicone, glycerin, cationic polymer such as PVP, cellulose, docosanol, BTMS, behenyl alcohol and/or poloxamer. In a preferred embodiment, a base antimicrobial solution contains approximately 70% alcohol, 2% CHG and 28% USP purified water for skin prepping, and 0.12% CHG in alcohol for mouth disinfecting. One of skill in the art will appreciate that other ingredients, including those mentioned above, may be added to each of the base antimicrobial solutions to provide a desired antimicrobial or antiseptic agent 122 for a specific application.

In some embodiments, the reservoir 120 includes a neck portion 124 having a set of threads 126 for threadedly coupling to compatible threads 200 (not shown) located within the proximal end 112 of the body 110. In other embodiments, the reservoir 120 is coupled to the proximal end 112 of the body 110 via a pressure fit, a mechanical interface, or an adhesive.

The reservoir 120 further includes a membrane 128 or seal to retain the agent 122 within the reservoir 120 prior to coupling the reservoir 120 to the body 110. The membrane 128 generally comprises a foil seal that is applied to the opening 130 via an adhesive or heat sealing process. In some embodiments, the membrane 128 comprises a plastic-coated paper or cardboard material that is applied to the opening 130 in a similar fashion. The membrane 128 may also include a polymer material. Finally, in some embodiments portions of the membrane are scored 132 or otherwise weakened thereby encouraging the membrane 128 to break or defeat in a predictable manner.

In some embodiments, the proximal end 112 of the body 110 further comprises a feature (not shown) whereby the membrane 128 is punctured or otherwise defeated upon coupling the reservoir 120 to the body 110. For example, in some embodiments the proximal end 112 includes a spike 202 (see FIG. 2A), whereby upon threadedly coupling the reservoir 120 to the proximal end 112, the spike 202 punctures and displaces the membrane 128 to provide access to the antiseptic agent 122 within the reservoir 120. Alternatively, in other embodiments the membrane 128 is physically removed from the reservoir 120 prior to coupling the reservoir 120 and the body 110.

The distal end 114 of the body 110 includes an applicator 140. The applicator 140 comprises a non-woven material or foam sponge pad that is attached to the distal end 114 via an adhesive that is compatible with the antiseptic agent 122. The size and shape of the applicator 140 varies dependent upon the intended application of the antiseptic device 100. For example, the applicator 140 of the antiseptic device 100 is sized and shaped for use as either a mouth disinfectant device or a skin/surgical site disinfectant device.

Occasionally, the inner and/or outer surfaces of the mouth must be disinfected, for example, prior to the insertion of a respirator tube or other medical device into the mouth or throat. Accordingly, the shape and size of the applicator 140 is designed to compatibly insert within the mouth of a patient. For example, an applicator 140 for use as a mouth disinfectant device may include an elongated dome shape having a base diameter that is easily inserted into the patient's mouth. An elongated dome shape eliminates any right angles that may otherwise prevent thorough and even contact between the applicator 140 and the natural, curved surfaces of the inner mouth. Additionally, in some embodiments, the outer surface of the applicator 140 includes a small radius that permits application of the applicator to the inner and outer surfaces of a respirator tube or other medical device prior to inserting the device into the mouth of the patient.

Where the antiseptic device 100 is intended as a skin/surgical site disinfectant device, the shape and size of the applicator 140 is selected to provide a broad, flat surface to maximize contact between the applicator 140 and a generally flat skin surface. An example of such an applicator is shown and discussed in connection with FIG. 3B, below.

Figure 2A:
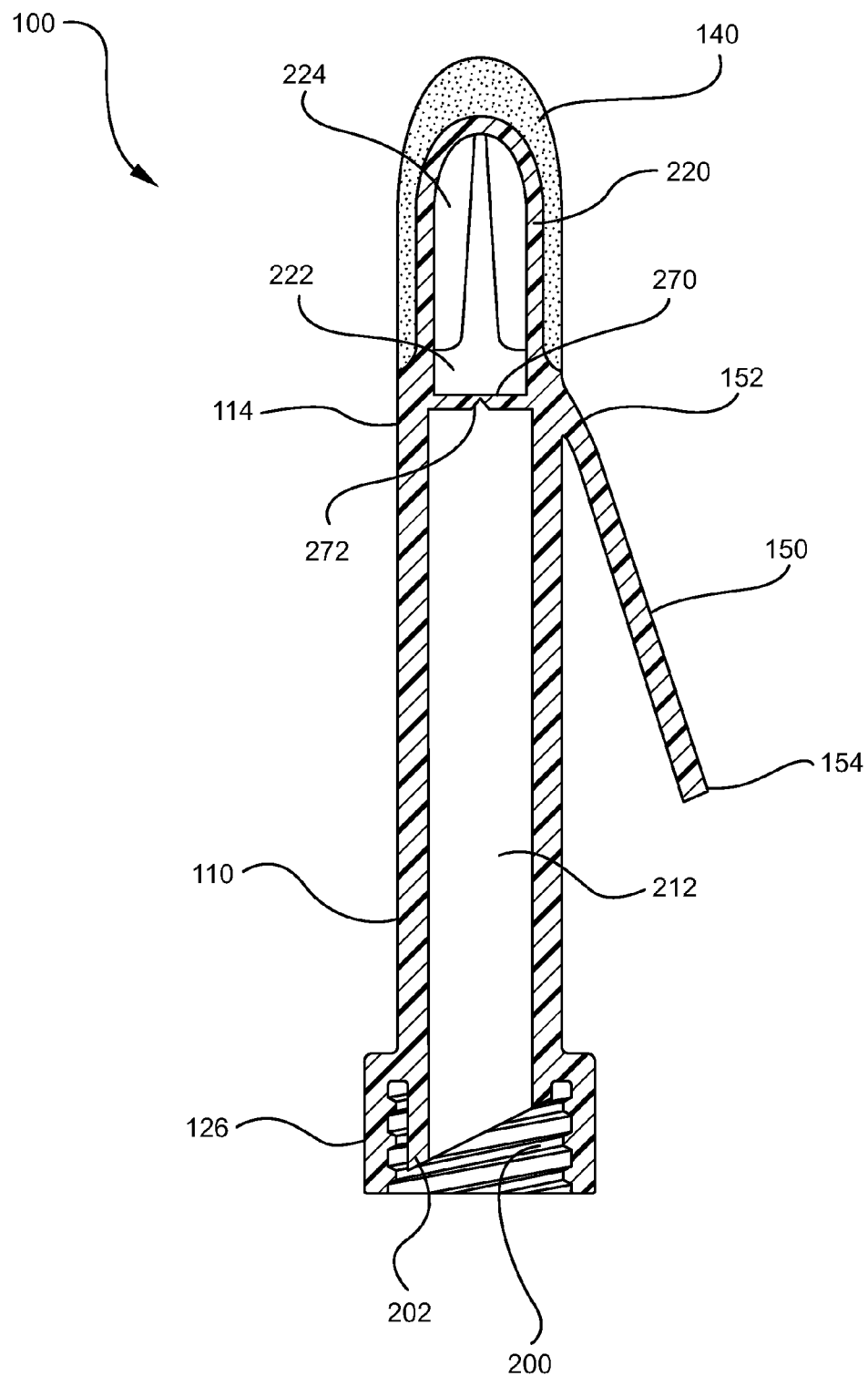
FIG. 2A is a cross-sectional view of an antiseptic applicator device prior to activation in accordance with a representative embodiment of the present invention.

In some embodiments, the antiseptic device 100 further comprises a handle 150. The handle 150 comprises a first end 152 coupled to the distal end 114 of the body 110 and a second end 154 which extends outwardly from the body 110. With reference to FIG. 2A, a cross-section view of the antiseptic device 100 is shown. The body 110 of the antiseptic device 100 comprises a hollow interior or lumen 212 for receiving and storing the antiseptic agent 122 from the reservoir 120. The body 110 further includes a fluid dispensing chamber 220. The fluid dispensing chamber 220 is located at the most distal end 114 of the body 110 and supports the applicator 140. In some embodiments, the fluid dispensing chamber 220 comprises a lumen 222 having a plurality of windows 224 through which the antiseptic agent 122 flows and is absorbed by the applicator 140. In other embodiments, the lumen 222 of the fluid dispensing chamber 220 comprises a plurality of holes, slits or other orifices.

Figure 2B:
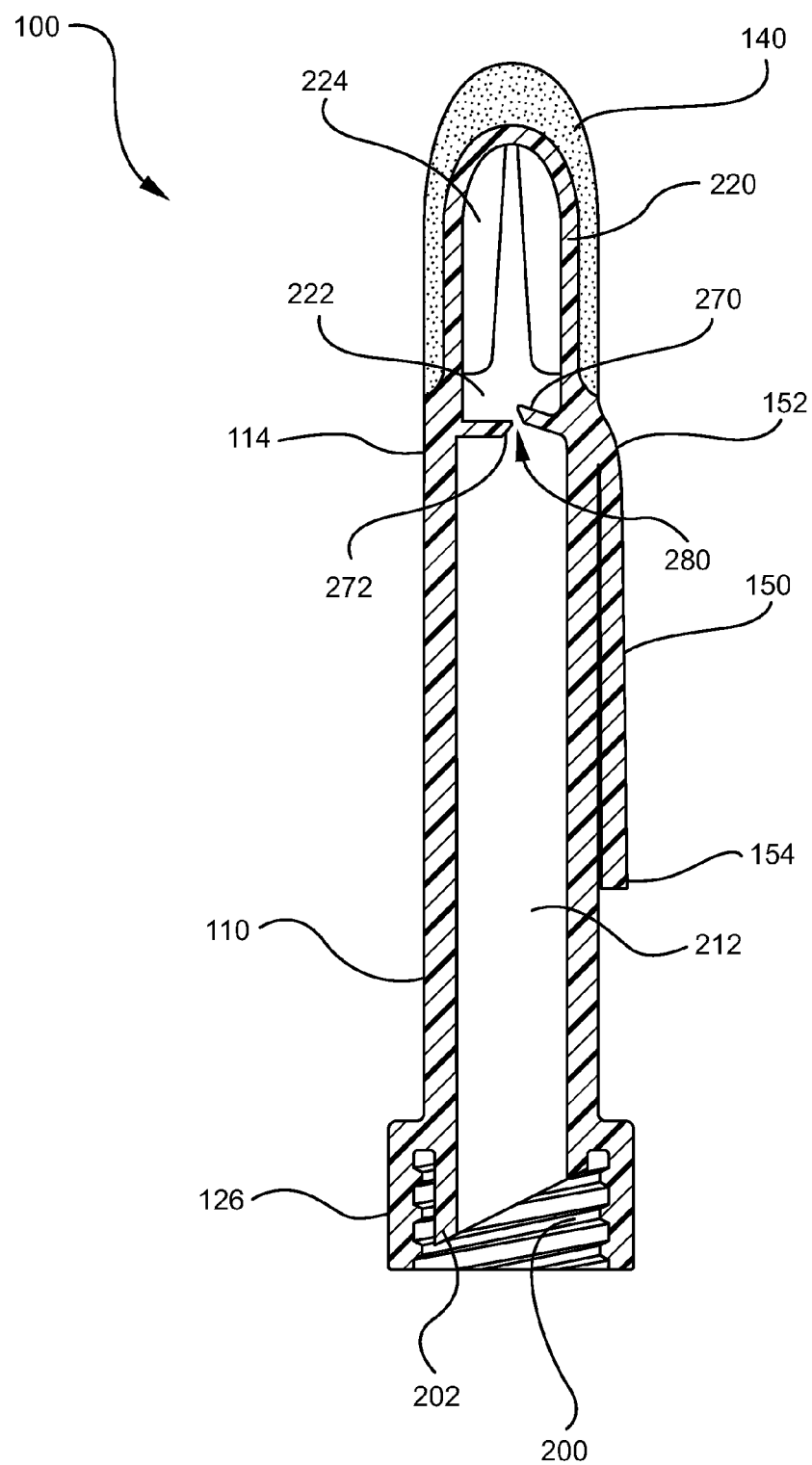
FIG. 2B is a cross-sectional view of an antiseptic applicator device following activation in accordance with a representative embodiment of the present invention.

In some embodiments, a breakable membrane 270 is interposed between the interior lumen 212 and the fluid dispensing chamber 220 of the body 110. The membrane 270 is provided to prevent fluid communication between the lumen 212 and the fluid dispensing chamber 220. A portion of the membrane 270 is scored 272 or otherwise weakened to encourage the membrane 270 to break or defeat in a predictable manner. In some embodiments, the membrane 270 is located opposite the first end 152 of the handle 150. Accordingly, as the handle 150 is actuated towards the body 110 from a closed position to an open position, the first end 152 of the handle 150 applies a torque force to the membrane 270 thereby causing the membrane 270 to defeat along the scored 272 portion, as shown in FIG. 2B. Once defeated, an opening 280 is provided through the membrane 270 such that the lumen 212 and the fluid dispensing chamber 220 are in fluid communication.

Figure 3A:
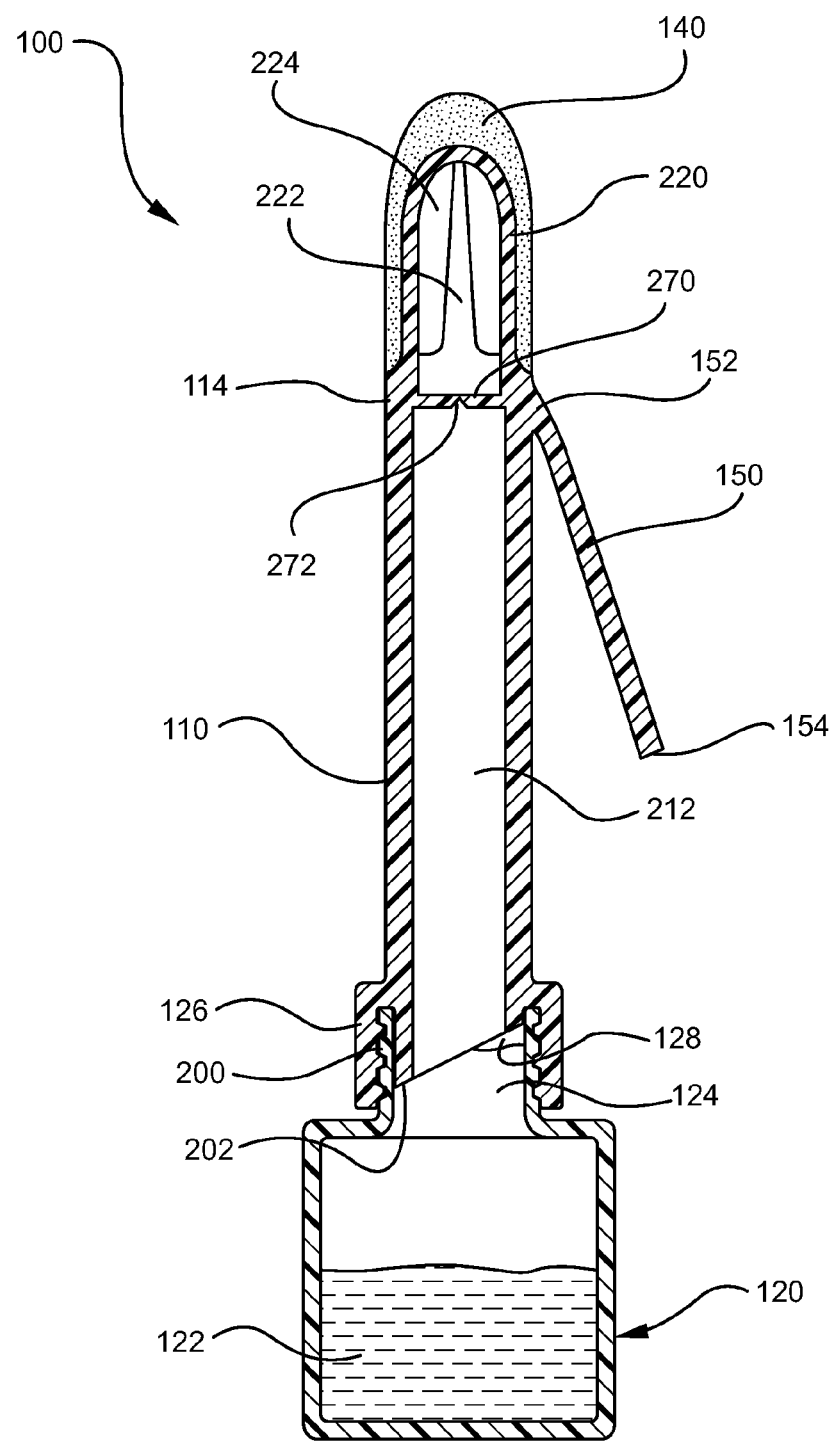
FIG. 3A is a cross-sectional view of an antiseptic applicator device prior to activation as coupled to a fluid reservoir in accordance with a representative embodiment of the present invention.

Referring now to FIG. 3A, a cross-section view of the antiseptic device 100 is shown coupled to a cross-sectioned reservoir, prior to actuating the handle 150. As previously discussed, as the antiseptic device 100 is coupled to the reservoir 120 the spike feature 202 punctures the membrane 128 to provide fluid communication between the reservoir 120 and the inner lumen 212 of the body 110. Thus, once the membrane 128 is defeated, the antiseptic device 100 and attached reservoir 120 are inverted to permit the antiseptic agent 122 to flow into the inner lumen 212 of the body 110. However, prior to actuating the handle 150 to a closed position, the antiseptic agent 122 is substantially prevented from bypassing the membrane 272 and flowing into the fluid dispensing chamber 220.

Figure 3B:
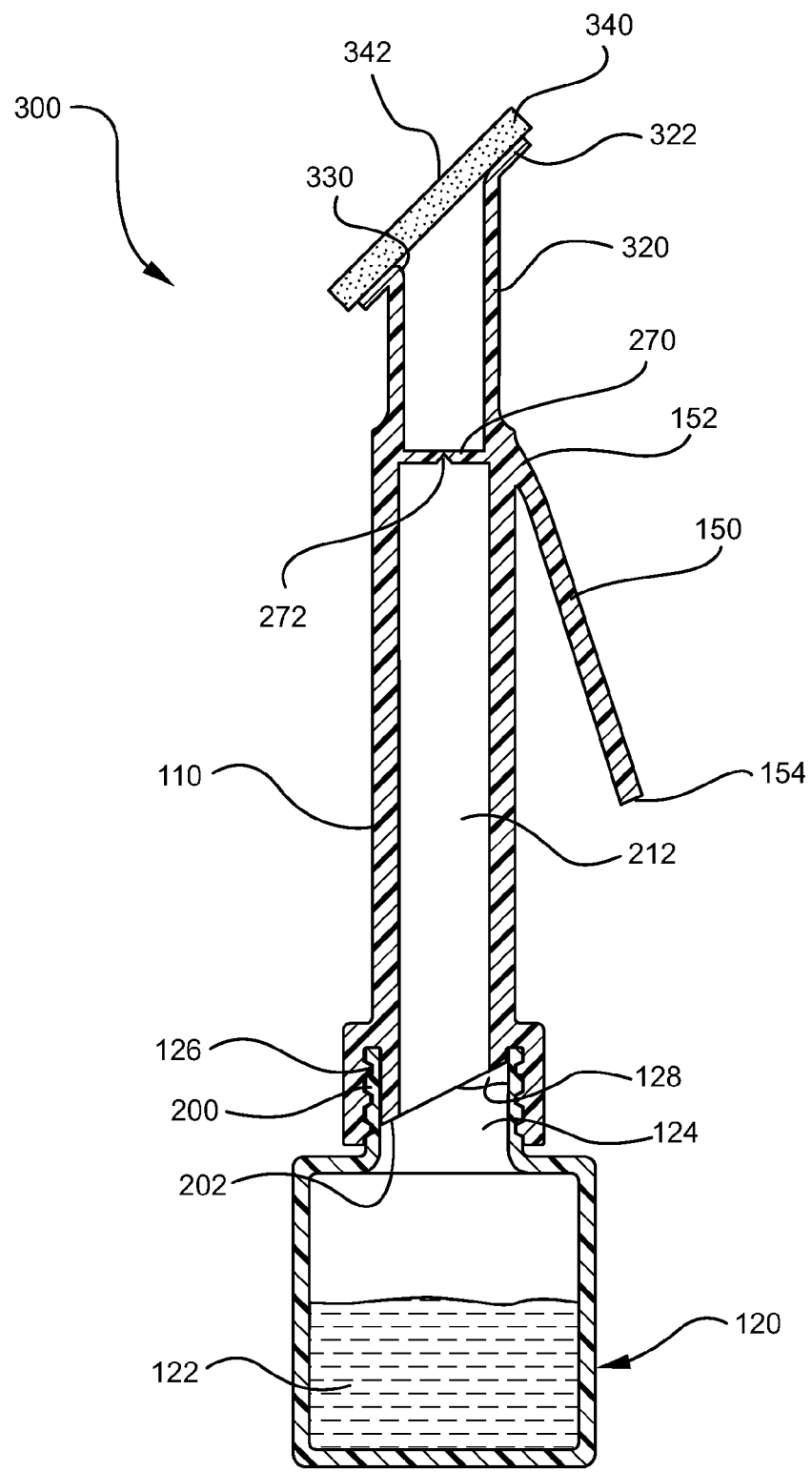
FIG. 3B is a cross-sectional view of an antiseptic applicator device prior to activation as coupled to a fluid reservoir in accordance with a representative embodiment of the present invention.

Referring now to FIG. 3B, a cross-section view of an antiseptic device 300 is shown coupled to a cross-sectioned reservoir, prior to actuating the handle 150. In the process of coupling the device 300 to the reservoir 120, the spike feature 202 pierces, punctures or otherwise defeats the membrane 128 to provide fluid communication between the reservoir 120 and the inner lumen 212 of the device body 110.

Antiseptic device 300 is modified to include a flat, linear applicator 340 having a broad surface for applying the antiseptic agent 122 to a generally flat surface. For this embodiment, the fluid dispensing chamber 320 generally comprises a tubular shape having an angled, terminal end surface 322 configured to receive the flat applicator 340. An opening 330 between the fluid dispensing chamber 320 and the applicator 340 permits fluid within the dispensing chamber 320 to contact the applicator 340 and to be absorbed thereby.

Applicator 340 comprises a non-woven material or foam sponge pad that is sized and textured for applying the antiseptic agent 122 to a desired surface. For example, in some embodiments applicator 340 includes an abrasive outer surface 342 to assist in exfoliation or debridement of a skin surface. In other embodiments, applicator 340 includes an abrasive outer surface to assist in scrubbing and disinfecting an object, such as a piece of machinery or a surface such as a table or bed surface. And in some embodiments, applicator 340 includes a smooth outer surface for applying the antiseptic agent 122 to disinfect a surface without harsh scrubbing.

In some embodiments, the terminal end surface 322 is angled relative to body portion 110 of the antiseptic device 300. Accordingly, when the applicator 340 is coupled to the terminal end surface 322, the applicator 340 is also angled relative to the applicator body 110. The angle of the applicator 340 is selected to assist a user in contacting a surface with the applicator 340 while holding the body portion 110 of the device in an ergonomically effective position. Furthermore, the position and length of the body portion 110 is selected to provide a gripping surface to the device 300 and remove the user's hand from the area proximal to the applicator 340. As such, the handle function of the body portion 110 provides the user with control over the device 300 while preventing undesired exposure and/or contamination to the treatment site or surface.

Figure 4:
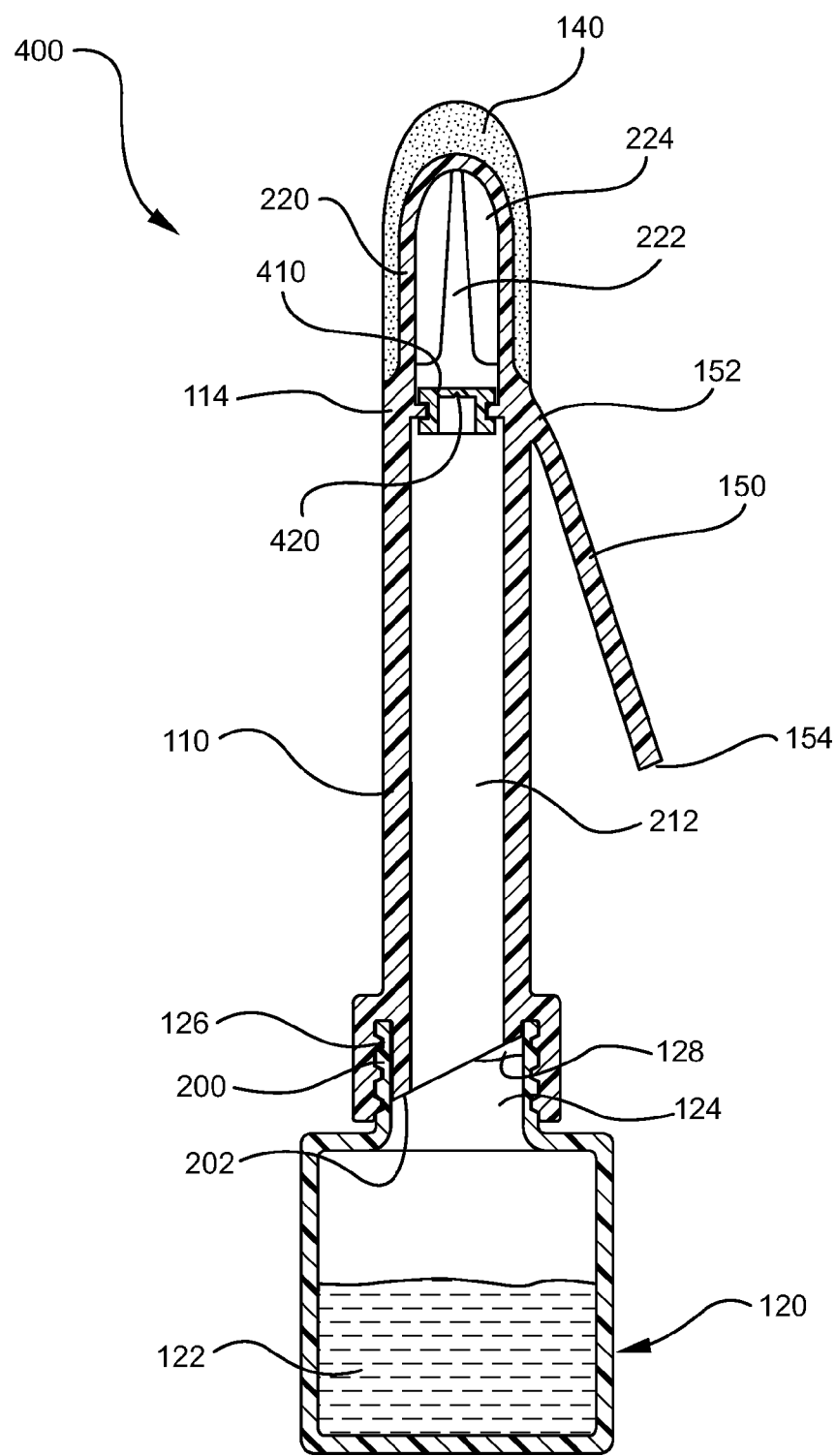
FIG. 4 is a cross-sectional view of an antiseptic applicator device including a one-way valve in accordance with a representative embodiment of the present invention.

Referring now to FIG. 4, a cross-section view of an antiseptic device 400 is shown coupled to a cross-sectioned reservoir 120. In some embodiments, a one-way valve 410 is interposed between the fluid dispensing chamber 220 and the inner lumen 212 of the device 400. The one-way valve 410 generally comprises a flexible or semi-flexible polymer material that is secured within a constricted portion of the inner lumen 212. In some embodiments, the valve 410 includes a duck bill or an umbrella valve. In other embodiments, the valve 410 includes a slit 420 that is biased to a closed position so as to prevent fluid communication between the fluid dispensing chamber 220 and the inner lumen 212. However, when a pressure within the inner lumen 212 exceeds the threshold pressure of the one-way valve 140, the one-way valve 410 is defeated such that the slit 420 opens to provide fluid communication between the inner lumen 212 and the fluid dispensing chamber 220.

For example, in some embodiments the body portion 110 of the device 400 comprises a semi-flexible tubing material capable of being compressed or squeezed by the user. Thus, as the user compressed the body portion 110, the pressure within the inner lumen 212 increases to exceed the threshold pressure of the one-way valve 140. When this occurs, the one-way valve 410 is defeated and the antiseptic agent 122 is permitted to bypass the valve 410, via the slit 420, and flow into the fluid dispensing chamber 220. When the pressure subsides, the valve closes to prevent further flow into the dispensing chamber 220. In some embodiments, the one-way valve 410 is replaced with a mechanical valve that the user directly manipulates, such as a flapper or sliding valve. In other embodiments, the breakable membrane is replaced with a small hole that would allow antiseptic agent 122 to flow from the inner lumen 212 into the dispensing chamber 220 when the body portion 110 is compressed. However, fluid would not be permitted to flow without compression due to the inner lumen being unvented and due to the surface tension of the antiseptic agent 122.

While applying positive pressure to the body portion 110 of the device 400 is one method to defeat the valve 410, one of skill in the art will appreciate that other methods may be used to equally defeat the valve 410. For example, in some embodiments, the fluid dispensing chamber 220 is modified to include a vacuum source whereby the pressure within the fluid dispensing chamber 220 is decreased below the threshold pressure of the one-way valve 410. In other embodiments, the reservoir 120 comprises a syringe (not shown) containing an antiseptic agent 122. As the syringe is compressed, the antiseptic agent 122 is injected into the inner lumen 212 thereby increasing the pressure within the inner lumen 212. When the pressure within the inner lumen 212 exceeds the threshold pressure of the one-way valve 410, the valve 410 is defeated and the antiseptic agent 122 flows into the fluid dispensing chamber 220 via the opened slit 420.

Figure 5A:
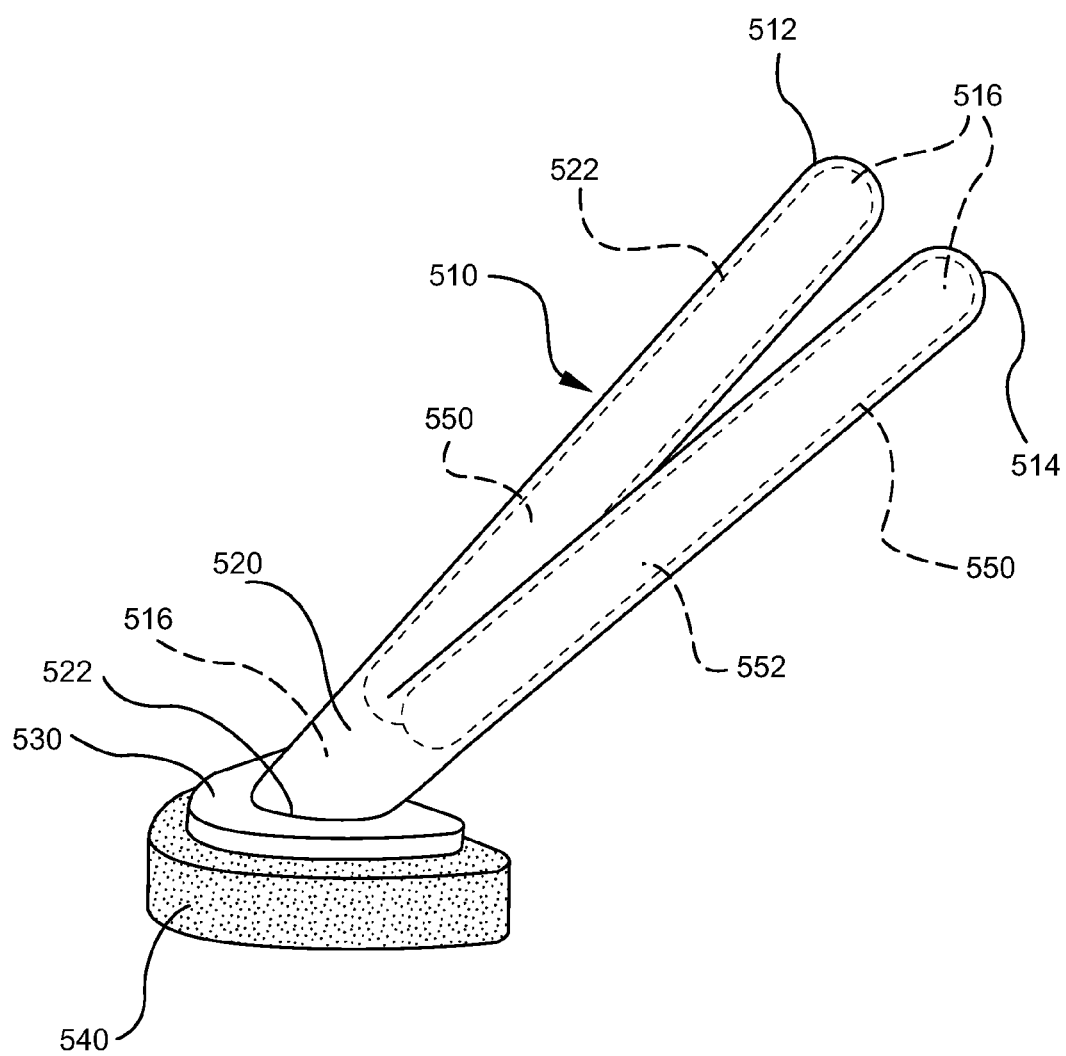
FIG. 5A is a perspective view of a two-handled antiseptic applicator device in accordance with a representative embodiment of the present invention.

Referring now to FIGS. 5A-8, various embodiments of a two-handled antiseptic device are shown. With reference to FIG. 5A, a perspective view of a two-handled device 500 is shown. A two-handled device 500 in accordance with the present invention generally comprises a bifurcated body 510, wherein each half of the body forms an opposing handle. A conjoined portion 520 of the body 510 forms the terminal end 522 of the body 510, and is coupled to a mounting plate 530. The mounting plate 530 provides a generally planar surface to which is attached an applicator 540.

The bifurcated body 510 includes a first handle 512 and a second handle 514. The bifurcated body 510 further includes an inner lumen 516 which is comprised of interconnected lumens located within the first handle 512, the second handle 514 and the conjoined portion 520. In some embodiments, a portion of the inner lumen 516 is configured to receive an ampoule or phial 550 containing a desired antiseptic agent 552. For example, in some embodiments portions of the lumen 516 located in each handle 512, 514 are configured to receive a phial 550 containing an antiseptic agent 552.

The antiseptic agent 552 is released from each phial 550 as the phial 550 is broken within the respective portion of the lumen 516. In some embodiments, the bifurcated body 510 comprises a semi-flexible polymer material that is capable of being compressed or flexed by the hand of the user. When the user compresses a single handle, for example handle 512, the phial 550 contained within the handle 512 is broken thereby releasing the antiseptic agent 552 from the phial 550 and into the inner lumen 516. Alternatively, when the user grasps and compresses both handles together, the phial 550 contained within each handle 512 and 514 is broken thereby releasing the antiseptic agent 552 from each phial 550 and into the inner lumen 516. Thus, the breakable material of the phial 550 serves as a barrier between the antiseptic agent 552 and the inner lumen 516.

Figure 5B:
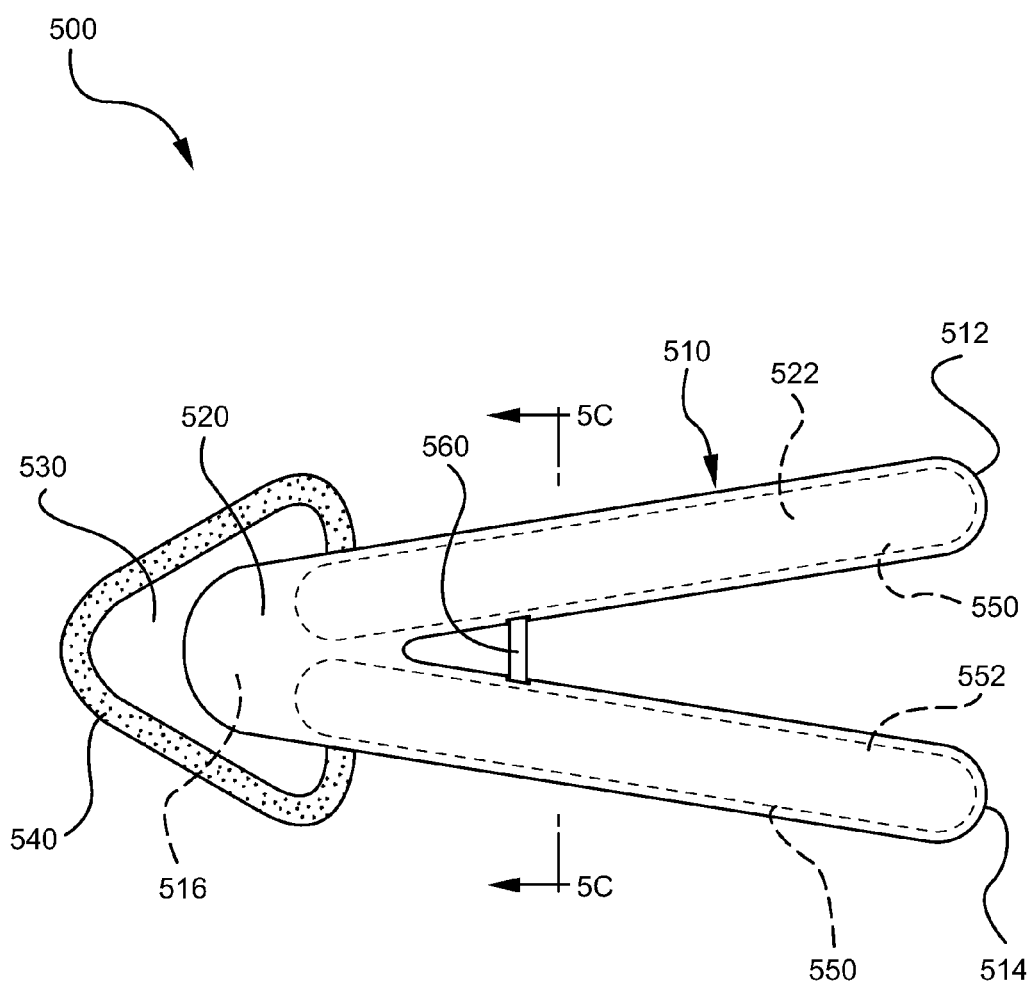
FIG. 5B is a top view of a two-handled antiseptic applicator device in accordance with a representative embodiment of the present invention.

Referring now to FIG. 5B, a top view of a two-handled device 500 is shown. In some embodiments, the bifurcated body 510 further includes a wedge point 560 interposedly positioned between the opposing handles 512 and 514. The wedge point 560 generally comprises a rigid feature having a tensile strength greater than the tensile strength of the phial 550 material. In some embodiments, the wedge point 560 is positioned between the opposing handles such that when the handles 512 and 514 are closed or brought together, the wedge point 560 is pinched between the opposing handles resulting in the wedge point 560 breaking the phials 550.

Figure 5C:
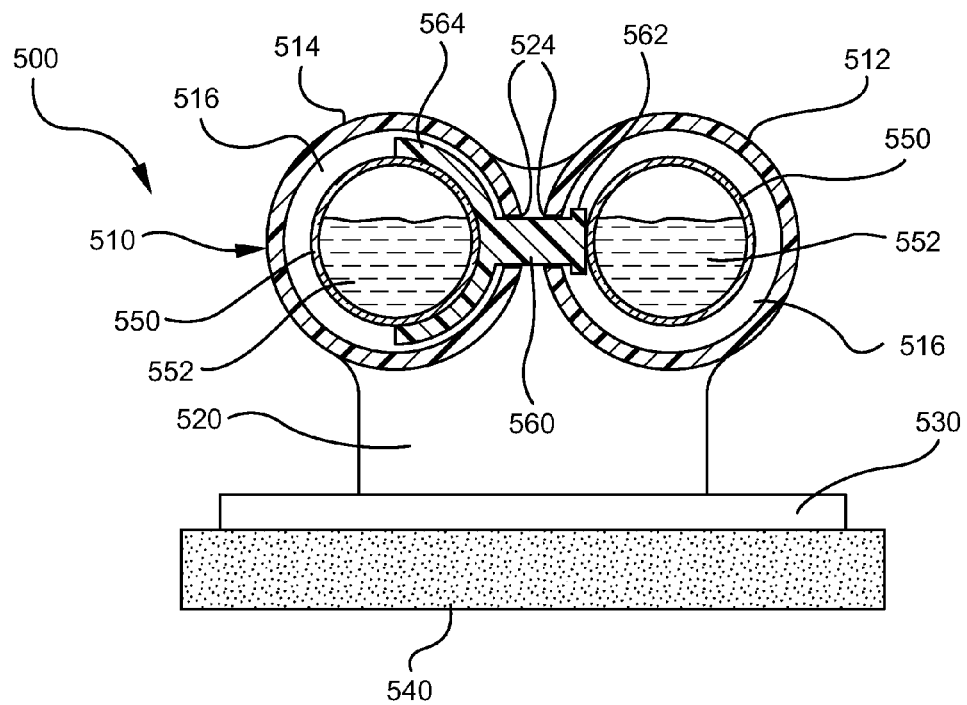
FIG. 5C is a cross-sectioned rear view of a two-handled antiseptic applicator device in accordance with a representative embodiment of the present invention.

With reference to FIG. 5C, a cross-section rear view of the two-handled device 500 is shown. In some embodiments, adjacent inner surfaces of the opposing handles 512 and 514 include access windows 524 through which a middle portion of the wedge point 560 is positioned. The access windows 524 are generally configured to provide passage for the middle portion of the wedge point 560 yet prevent passage of fluid located within the lumen of each handle 512 and 514. The wedge point 560 comprises a first end 562 located within the inner lumen of the first handle 512, and a second end 564 located within the inner lumen of the second handle 514. The first and second ends 562 and 564 are connected via the middle portion of the wedge point 560. In some embodiments, the first end 562 comprises a flat, anvil surface configured to directly abut the phial 550 within the first handle 512. The second end 564 comprises a concaved surface configured to directly receive the outer diameter of the phial 550 located in the second handle 514. Thus, as the first and second handles are closed or brought together, the wedge point 560 binds each phial 550 against the inner surface of each handle's outer wall. Continued closing of the handles 512 and 514 then forces the first and second ends 562 and 564 of the wedge point 560 through their respective phials 550 thereby releasing the antiseptic agents 552 contained therein.

Figure 5D:
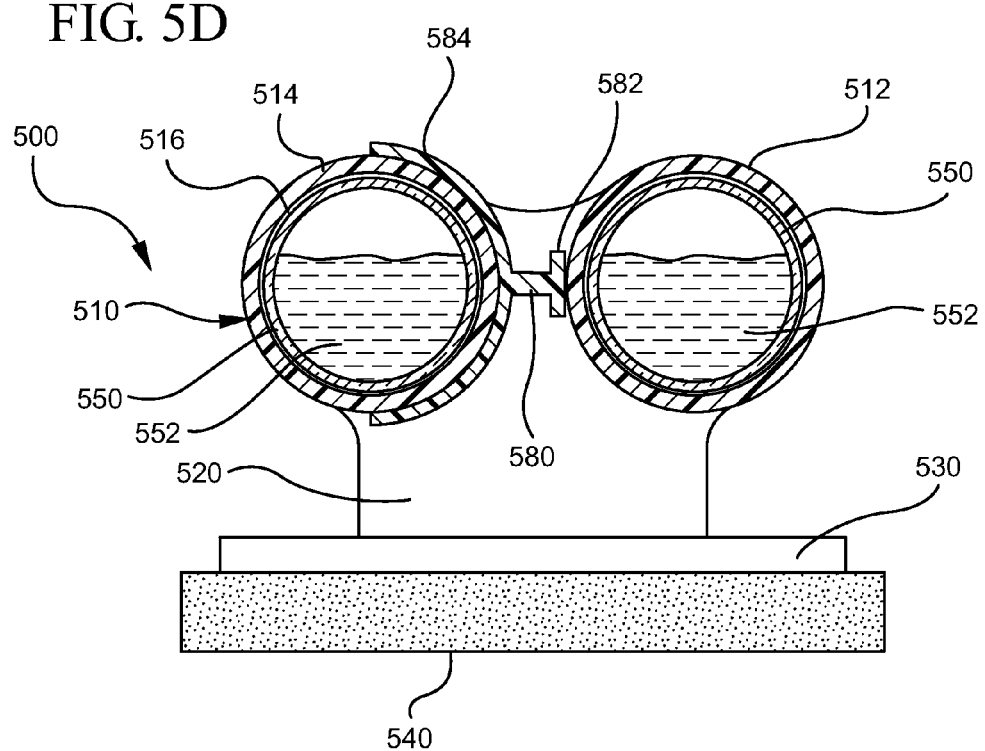
FIG. 5D is a cross-sectioned rear view of a two-handled antiseptic applicator device in accordance with a representative embodiment of the present invention.

Referring now to FIG. 5D, an alternate embodiment of wedge point 560 is shown. For this embodiment, the first end 582 and second end 584 of wedge point 580 are configured to couple to the external surfaces of opposing handles 512 and 514. Accordingly, as the first and second handles are closed or brought together, the wedge point 560 immobilizes the inner portions of the exterior surface thereby causing the phials 550 to be compressed and crushed between the interior surface of each handle's outer wall and the interior surface of each handle's inner wall.

Figure 6A:
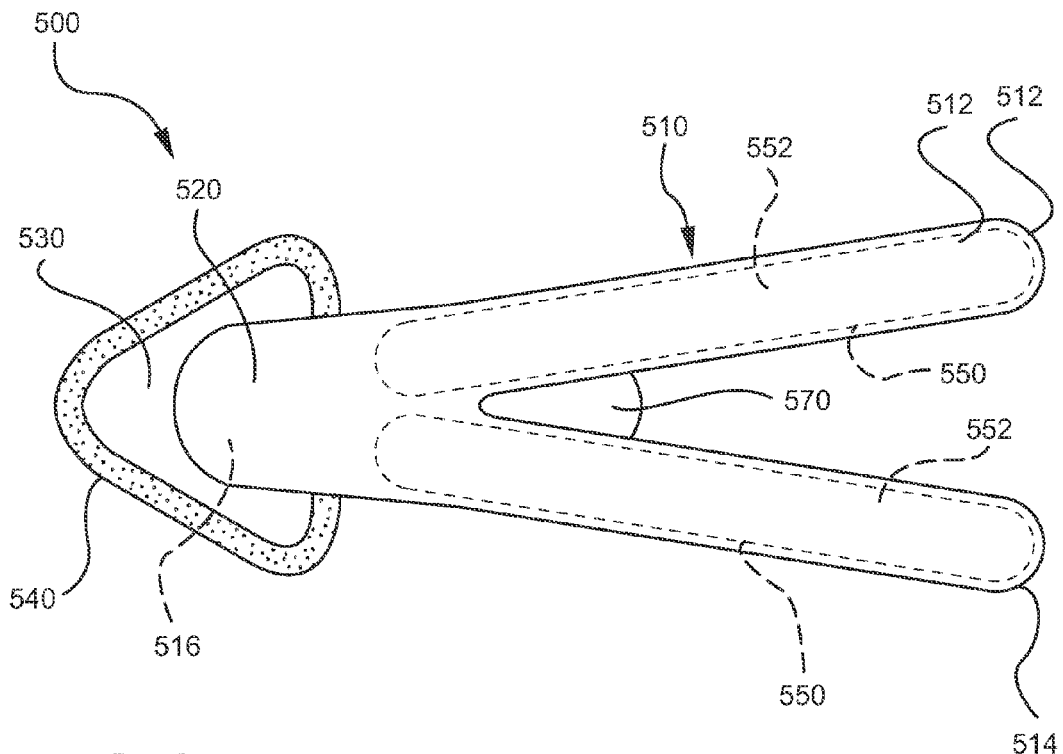
FIG. 6A is a top view of a two-handled antiseptic applicator device in accordance with a representative embodiment of the present invention.
Figure 6B:
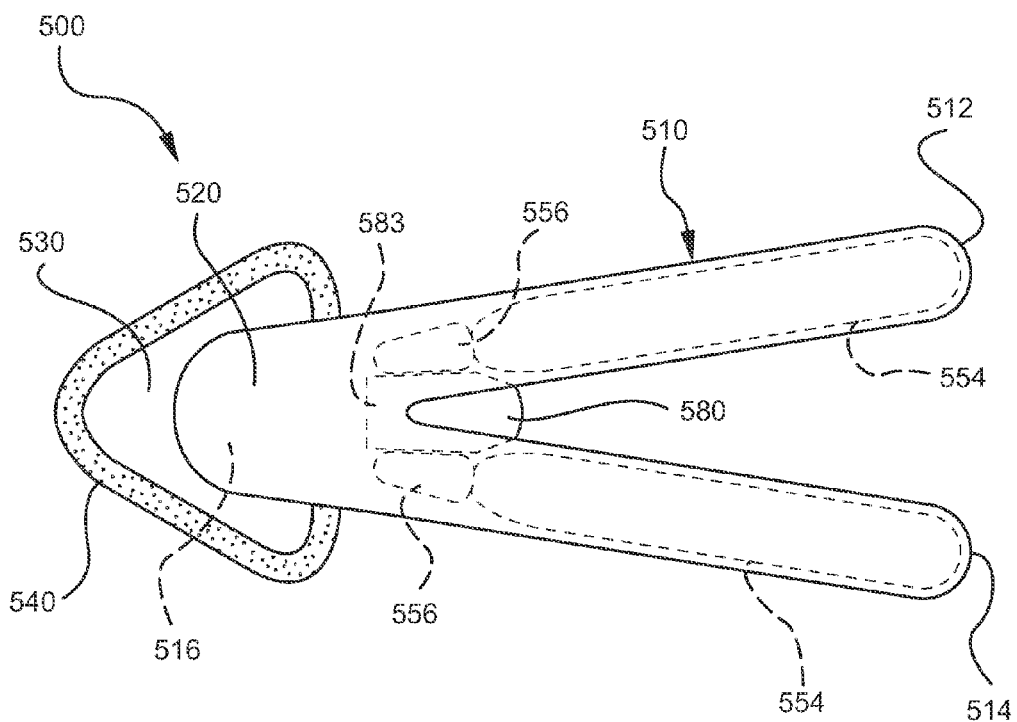
FIG. 6B is a top view of a two-handled antiseptic applicator device in accordance with a representative embodiment of the present invention.

Referring now to FIG. 6A, an alternate embodiment of the wedge point is shown. For this embodiment, wedge point 570 is a molded, webbed extension linking the first and second handles 512 and 514 adjacent to the conjoined portion 520 of the body 510. In some embodiments, wedge point 570 is formed during the molding process of the device body 510, wherein a mold used to form the body 510 includes a void to receive a sufficient amount of material to form the wedge point 570. In other embodiments, wedge point 570 is formed or molded in a separate process and subsequently coupled to the opposing handles 512 and 514 via an appropriate method, such as plastic welding, an adhesive, or interlocking features/surfaces.

In some embodiments, a wedge point 580 is provided having wing features 583 for applying force to a specific portion of the phials 554. Some phials 554 include a scored surface 556 to encourage or control how the phial 554 is broken. Accordingly, in some embodiments the wedge point 580 includes winged features 583 that are designed to contact the phials 554 so as to break the phial 554 along the scored surface 556. The winged features 583 may include a molded feature of the device body 520, a separate device, or a combination of a molded feature and a separate device.

In some embodiments, each phial 554 contained within the handle portion of the inner lumen 516 may contain the same or different solutions. Different solutions may be useful for procedures requiring a two-step preparation. For example, in some embodiments phial 554 of the first handle 512 contains a detergent solution, while phial 554 of the second handle 514 contains a disinfectant solution. A method for utilizing different solutions may include: 1) Breaking a first phial to release a first solution, wherein the first solution is a detergent to thoroughly wash and clean at and around an incision site to remove gross contamination before performing antiseptic skin preparation; and 2) Breaking a second phial to release a second solution, wherein the second solution is an appropriate antiseptic agent for skin preparation.

Figure 7A:
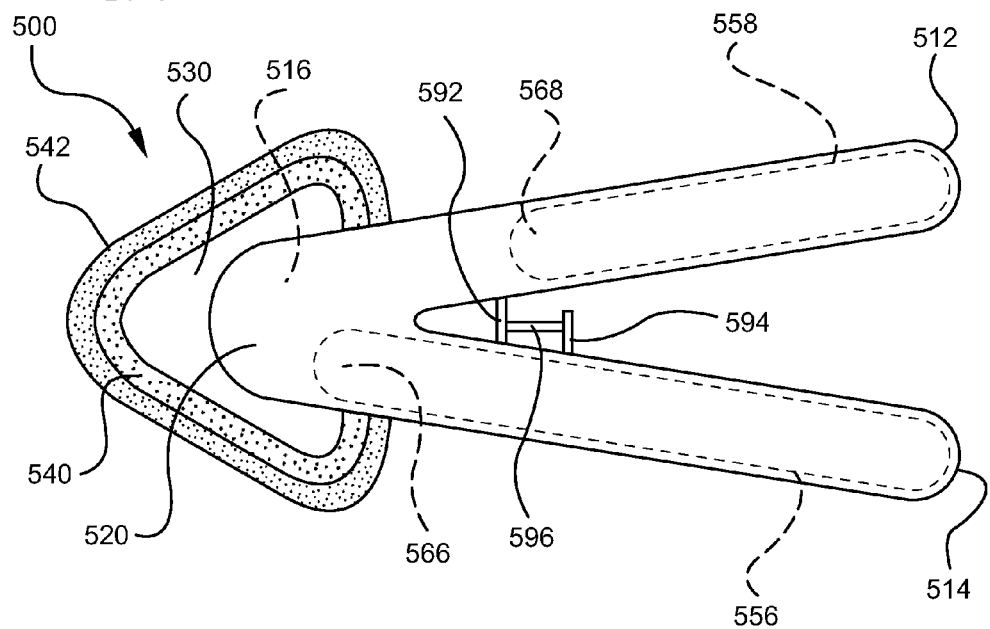
FIG. 7A is a top view of a two-handled antiseptic applicator device having a multistep wedge point in accordance with a representative embodiment of the present invention.
Figure 7B:
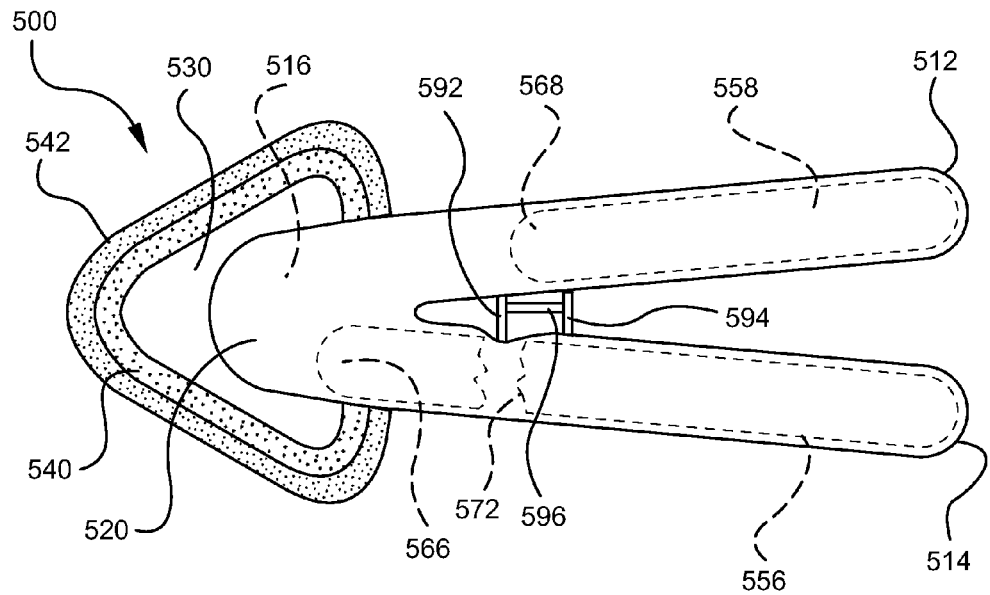
FIG. 7B is a top view of a two-handled antiseptic applicator device having a multistep wedge point following breakage of the first phial in accordance with a representative embodiment of the present invention.
Figure 7C:
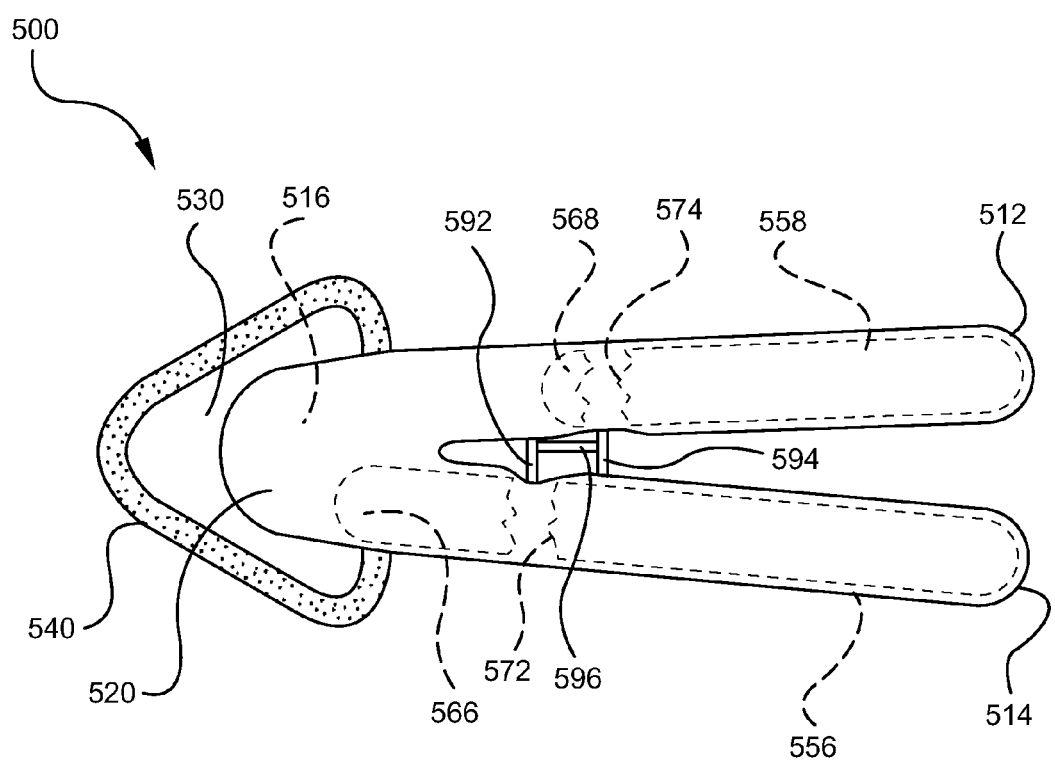
FIG. 7C is a top view of a two-handled antiseptic applicator device having a multistep wedge point following breakage of the second phial in accordance with a representative embodiment of the present invention.

With reference to FIGS. 7A-7C, a device 500 is shown housing a first phial 556 containing a first solution, and a second phial 558 containing a second solution. Device 500 further includes a multistep wedge point 590 interposedly positioned between the first handle 512 and the second handle 514. Finally, device 500 includes a layered applicator including a first applicator 542 and a second applicator 540.

The multistep wedge point 590 comprises a first contact 592 coupled to a second contact 594 via a spacer 596. The first contact 592 is positioned adjacent to the conjoined portion 520 of the body so as to abut only the first phial 556. In some embodiments, the first and second phials 556 and 558 are positioned within the handles 512 and 514 such that the distal end 566 of the first phial 556 overlaps the distal end 568 of the second phial 558. The spacer 596 length is selected to provide a distance between the first contact 592 and the second contact 594 such that the first contact 592 is positioned adjacent to distal end 566 of the first phial 556, and the second contact 594 is positioned adjacent to distal end 568 of the second phial 558. Thus, upon moving the handles 512 and 514 to a partially closed position, as shown in FIG. 7B, the first contact 592 of the multistep wedge point 590 is driven into the distal end 566 of the first phial 556. As the first phial 556 is pinched between the first contact 592 and the interior surface of the second handle 514, the phial 556 is defeated or broken 572 thereby releasing the first solution.

In some embodiments, the first solution comprises a detergent for removing gross contaminants from a desired surface. Accordingly, in some embodiments the device 500 includes a first applicator 542 that is sized and textured for scrubbing or otherwise applying the detergent solution to the desired surface. Following complete application of the first solution, the first applicator 542 is removed from the device 500 to reveal the uncontaminated second applicator 540. The first applicator 542, including the gross contaminants contained thereon, is then discarded.

Following removal of the first applicator 542, the opposing handles 512 and 514 are moved to a fully closed position, as shown in FIG. 7C. In this position, the second contact 594 of the multistep wedge point is driven into the distal end 568 of the second phial 558. As the second phial 558 is pinched between the second contact 594 and the interior surface of the first handle 512, the phial 558 is defeated or broken 574 thereby releasing the second solution.

In some embodiments, the second solution comprises an antiseptic solution for cleaning or otherwise removing pathogens from a desired surface. Accordingly, in some embodiments the second applicator 540 is sized and textured for scrubbing or otherwise applying the antiseptic solution to the desired surface. Following complete application of the second solution, the device 500 is discarded.

Figure 8:
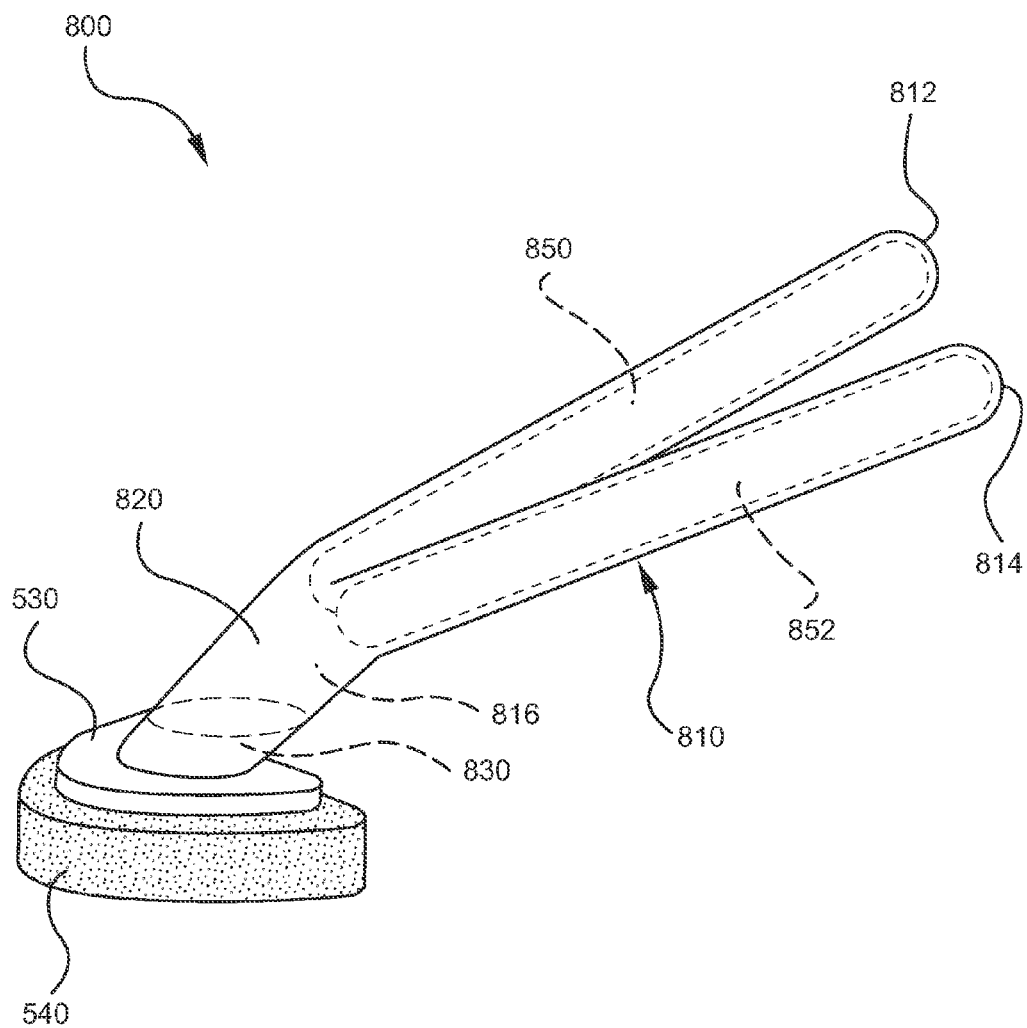
FIG. 8 is a perspective view of a two-handled antiseptic applicator device having an elongated conjoined portion and angled handles in accordance with a representative embodiment of the present invention.

Referring now to FIG. 8, an alternate embodiment of the two-handled device 800 is shown. In some embodiments, the body 810 of the two-handled device 800 further includes an elongate conjoined portion 820, wherein the handles 812 and 814 are coupled to the conjoined portion 820 at a desired angle. The elongate conjoined portion 820 increases the volume of the inner lumen 816 thereby accommodating an increased volume of antiseptic agent 852. Additionally, the increased volume permits placement of a sponge or filter 830 to prevent broken glass from entering the applicator 540.

In some embodiments, the desired angle of the opposed handles 812 and 814 is selected to accommodate a user in optimally contacting a desired surface with the applicator 540 while holding the handles 812 and 814 in an ergonomically effective position. The combination of the angled handles 812 and 814 and the elongate conjoined portion 820 further provide increased spacing between the user's hands and the applicator 540. This increased spacing is beneficial to prevent undesirable contamination of the applicator 540 and the treatment surface by the user's hands. Accordingly, in some embodiments it is desirable to optimize the length of the conjoined portion 820 and the angle of the handles 812 and 814 to provide a device 800 that is effective for sanitizing a desired surface and provides an ergonomic grip.

In other embodiments, the size and length of the opposing handles 812 and 814 is configured to adapt the device 800 for a specific procedure or gripping technique. For example, for some procedures a large volume of antiseptic agent is needed thereby requiring that the size of the opposing handles 812 and 814 be increased. Furthermore, where a user desires to hold the device 800 by pinching the device between their fingers, the size of the opposing handles 812 and 814 are decreased to ensure adequate control over the device by desired grip. In some embodiments, the outer surfaces of the opposing handles 812 and 814 are further modified to include textures and/or contours to facilitate a user's grip. Finally, where a user desires to grasp the device 800 in their hand, the size of the opposing handles 812 and 814 are increased to provide a greater gripping surface.

Figure 9A:
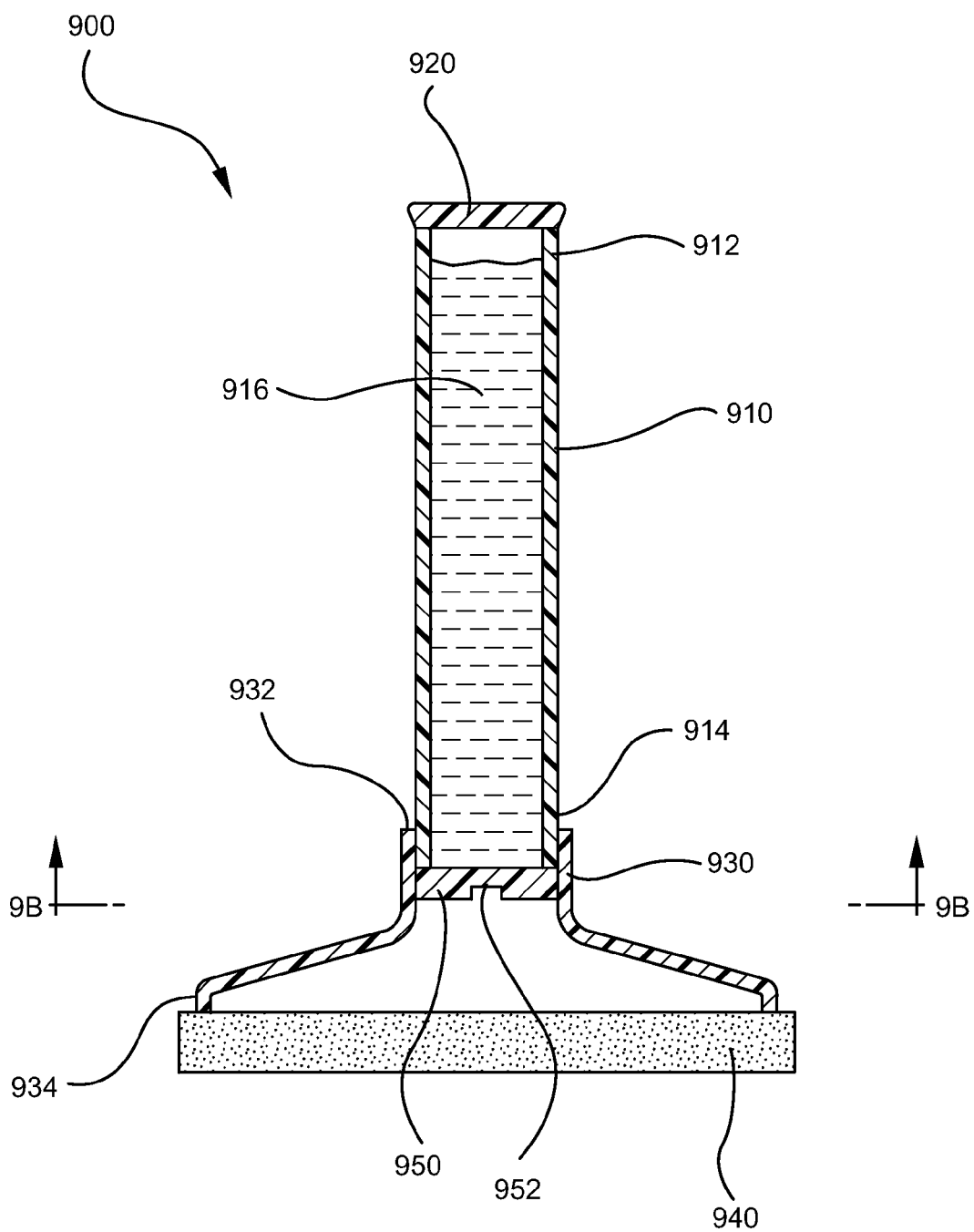
FIG. 9A is a cross-sectioned view of an antiseptic applicator device incorporating a scored membrane in accordance with a representative embodiment of the present invention.

With reference to FIG. 9A, an applicator device 900 is shown. The applicator device 900 comprises a fluid reservoir 910 having a proximal end 912 and a distal end 914. The proximal end 912 includes a cap 920 that seals or otherwise closes the proximal end 912. The distal end 914 is coupled to a fluid dispensing chamber 930 having a first end 932 for receiving the distal end 914 of the fluid dispensing chamber 930, and a second end 934 for supporting an applicator pad 940. A rupturable or breakable membrane 950 is interposed between the fluid reservoir 910 and the fluid dispensing chamber 930, thereby preventing the antiseptic agent 916 from flowing into the fluid dispensing chamber 930 prior to defeating the membrane 950.

The device 900 is prepared by filling the reservoir 910 with a desired antiseptic agent 916. After filling the reservoir 910, the cap 920 is placed on the proximal end 912 of the reservoir 910 to seal the agent 916 within the reservoir 910. In some embodiments, the cap 920 is formed by heat pressing the proximal end 912 of the reservoir 910 thereby forming a seal.

In some embodiments, the membrane 950 is disk-shaped having a uniform depression or scoring 952 that is broken or defeated by applying lateral force to the membrane 950. For example, in some embodiments the scoring 952 is broken by applying force to the applicator pad 940, whereby the force is transferred to the membrane 950 via the fluid dispensing chamber 930. In other embodiments, the scoring 952 is broken by compressing or squeezing the fluid reservoir 910 to increase the pressure within the reservoir 910 beyond the strength of the scored surface 952. Once defeated, the antiseptic solution 916 within the reservoir 910 flows through the membrane 950 and is absorbed by the applicator pad 940. The thickness of the membrane 950 and the depth of the scoring may be varied dependent upon the calculated force desired to defeat the membrane 950.

Figure 9B:
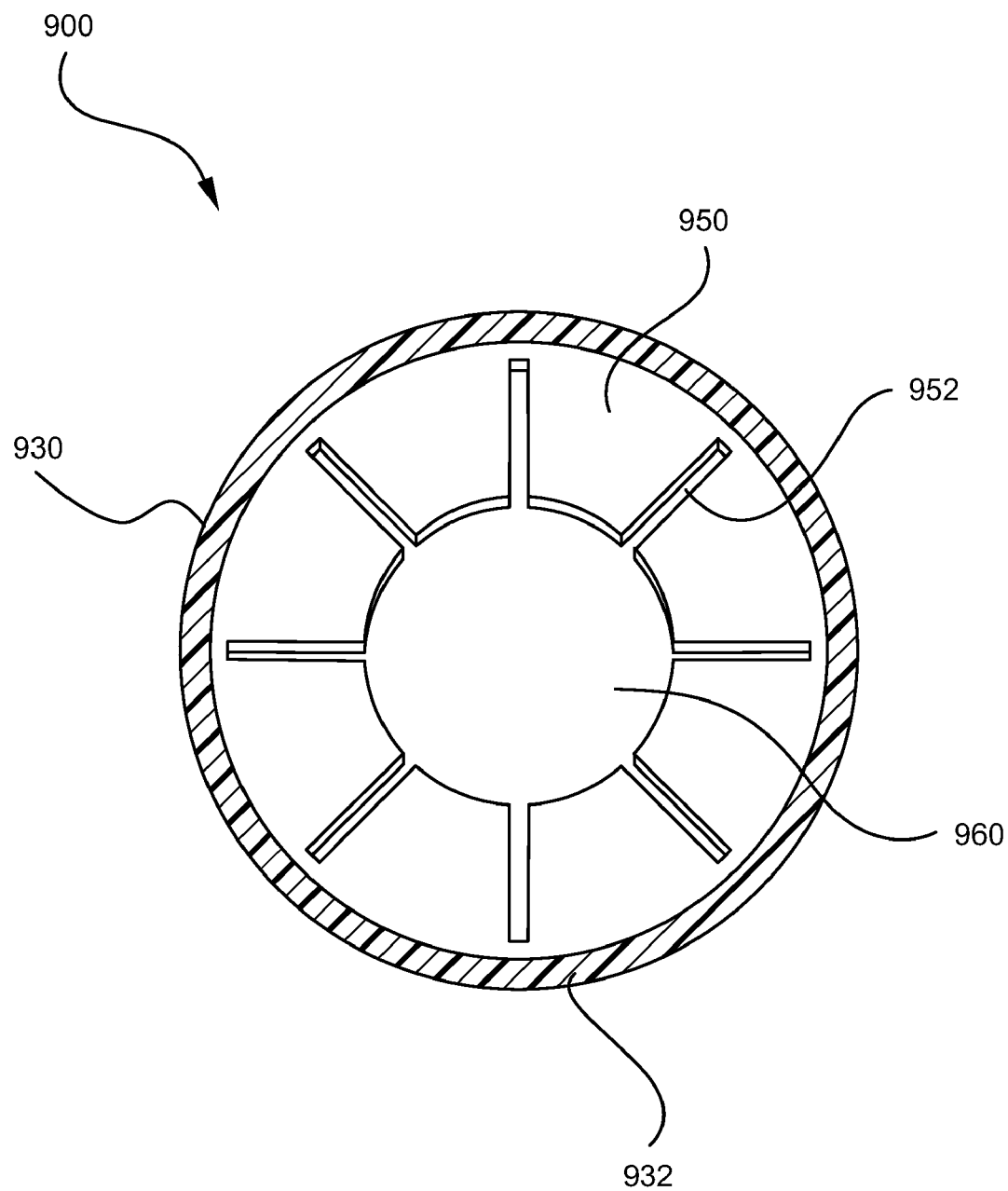
FIG. 9B is a cross-section view of FIG. 9A demonstrating a scored membrane in accordance with a representative embodiment of the present invention.

Referring now to FIG. 9B, the illustrated membrane 950 is disk-shaped and configured to compatibly seat within the proximal end 932 of the fluid dispensing chamber 930. In some embodiments, the scoring 952 comprises a webbed design featuring a plurality of scorings 960 having varying dimensions and breaking strengths. For example, in some embodiments portions of the membrane 950 are scored at varying depths or graduated depths to provide various breaking strengths across the membrane 950. Thus, when compressed with a lateral force along the reservoir 910, the membrane 950 breaks along some of the scored surface 952 and 960 to essentially form a gate valve. Since only some of the scored surfaces are defeated, the partially defeated membrane 950 controls flow of the antiseptic agent 916 through the membrane 950. However, upon apply additional lateral force to the reservoir 910, additional portions of the scored surfaces 952 and 960 are defeated thereby increasing the amount of antiseptic agent 916 permitted to flow through the membrane 950.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. An applicator device, comprising:
    a body comprising a pair of handles having a lumen;
    a reservoir comprising an ampoule, the reservoir being positioned within the lumen of the pair of handles, the reservoir containing an antiseptic agent;
    a pad coupled to the lumen; and
    a defeatable barrier forming a wall of the ampoule, wherein upon actuating the pair of handles the defeatable barrier is defeated and the antiseptic agent and the pad are in fluid communication via the lumen.

2. The device of claim 1, further comprising a wedge point interposedly positioned between the pair of handles, wherein upon actuation of the pair of handles, the wedge point defeats the defeatable barrier.

3. The device of claim 1, wherein the body comprises a semi-flexible material, wherein upon compressing the body the defeatable barrier is defeated.

4. A method for manufacturing an applicator device, comprising:
    providing a body comprising a pair of handles having a lumen;
    positioning a reservoir comprising an ampoule in the lumen of the pair of handles, the reservoir containing the antiseptic agent;
    coupling a pad to the lumen; and
    providing a defeatable barrier forming a wall of the ampoule, wherein upon actuating the pair of handles the defeatable barrier is defeated and the antiseptic agent and the pad are brought into fluid communication with each other via the lumen.

5. The method of claim 4, wherein the body comprises a semi-flexible material, wherein upon compressing the body the defeatable barrier is defeated.

6. An apparatus for applying an antiseptic to a surface, the apparatus comprising:
    a body comprising a first handle and a second handle, the first handle having a first inner lumen for storing a first reservoir containing a first antiseptic agent, and the second handle having a second lumen for storing a second reservoir containing a second antiseptic agent;
    an applicator pad coupled to the body and in fluid communication with the first and second inner lumens; and
    a wedge point interposed between the first and second handles, wherein upon activation of the handle, the wedge point opens at least one of the first and second reservoirs thereby releasing the antiseptic agent of the opened reservoir into a respective inner lumen and subsequently into contact with the applicator pad.

7. The apparatus of claim 6, wherein the first and second reservoirs are glass ampoules.

8. The apparatus of claim 6, wherein the wedge point is configured to open the first reservoir prior to opening the second reservoir.

* * * * *